US012765540B2

(12) United States Patent
Shang et al.

(10) Patent No.: US 12,765,540 B2
(45) Date of Patent: Oct. 20, 2026

(54) COMPOSITION FOR REMOVING PHOSPHOLIPIDS AND CELL DEBRIS AND METHOD FOR REMOVING PHOSPHOLIPIDS AND CELL DEBRIS ON BIOLOGICAL TISSUE

(71) Applicant: SHANGHAI NEWMED MEDICAL CO., LTD., Shanghai (CN)

(72) Inventors: Dapeng Shang, Shanghai (CN); Xiayan Yang, Shanghai (CN); Qifeng Yu, Shanghai (CN)

(73) Assignee: SHANGHAI NEWMED MEDICAL CO., LTD., Shanghai (CN)

( * ) Notice: Subject to any disclaimer, the term of this patent is extended or adjusted under 35 U.S.C. 154(b) by 452 days.

(21) Appl. No.: 18/369,824

(22) Filed: Sep. 18, 2023

(65) Prior Publication Data

US 2024/0000064 A1 Jan. 4, 2024

Related U.S. Application Data

(63) Continuation of application No. PCT/CN2022/081652, filed on Mar. 18, 2022.

(30) Foreign Application Priority Data

Mar. 31, 2021 (CN) ......................... 202110351059.5

(51) Int. Cl.

*A01N 1/128* (2025.01)
*A01N 1/124* (2025.01)
*C12N 5/00* (2006.01)

(52) U.S. Cl.

CPC ............ *A01N 1/128* (2025.01); *A01N 1/124* (2025.01); *C12N 5/0081* (2013.01)

(58) Field of Classification Search

CPC ...... A01N 1/128; A01N 1/124; C12N 5/0081; A61L 27/3625; A61L 27/3687; A61L 2430/20; A61L 2430/40; C11D 1/04; C11D 1/74; C11D 3/2006; C11D 3/2017; C11D 3/2068; C11D 7/261; C11D 7/263; C11D 7/3245; C11D 2111/12

See application file for complete search history.

(56) References Cited

FOREIGN PATENT DOCUMENTS

| | | | | |
|---|---|---|---|---|
| CN | 104705480 A | | 6/2015 | |
| CN | 110694112 A | * | 1/2020 | ......... A61L 27/3633 |

OTHER PUBLICATIONS

Li, Zhong,kui et al, CN-110694112-A machine translation, 12 pages. (Year: 2020).*

International Search Report of PCT Patent Application No. PCT/CN2022/081652 issued on Jun. 22, 2022.

* cited by examiner

*Primary Examiner* — Aaron J Kosar

(57) ABSTRACT

Disclosed in the present application is a composition for removing phospholipids and cell debris, comprising an alcohol, an alcohol ether, and a surfactant, wherein the alcohol accounts for 50-90 wt %, preferably 60-80 wt %; the alcohol ether accounts for 5-40 wt %, preferably 10-20 wt %; the surfactant accounts for 0.1-5 wt %, preferably 1-3 wt %. The present application further provides a method for removing phospholipids and cell debris on biological tissue. The composition of the present application is used for treating biological tissue, and the treated biological tissue has an excellent anti-calcification effect.

15 Claims, No Drawings

COMPOSITION FOR REMOVING PHOSPHOLIPIDS AND CELL DEBRIS AND METHOD FOR REMOVING PHOSPHOLIPIDS AND CELL DEBRIS ON BIOLOGICAL TISSUE

CROSS-REFERENCE TO RELATED APPLICATIONS

The present application is a continuation application of PCT application No. PCT/CN2022/081652 filed on Mar. 18, 2022, which claims the benefit of Chinese Patent Application No. 202110351059.5 filed on Mar. 31, 2021. The contents of all of the aforementioned applications are incorporated by reference herein in their entirety.

TECHNICAL FIELD

The present application relates to the field of biological tissues, and particularly to a composition for removing phospholipids and cell debris and a method for removing phospholipids and cell debris on biological tissue.

BACKGROUND

Biological valves are biomaterials used in the treatment of heart diseases. The main raw material of the current biological valve is pericardium, and the main reason for limiting the durability of the biological heart valve is that the pericardium is prone to calcification, causing the failure of the valve. The pericardial calcification is mainly due to pericardial phospholipids, cell and cell debris residues, exposed amino, carboxyl, and aldehyde groups in the pericardial molecular structure, and other calcification sites which are easy to react with calcium ions. In addition, the valve is damaged during multiple opening and closing processes, such that functional groups are exposed and calcification is also caused. However, there is no good method for removing phospholipids and cell and cell debris residues from the pericardium at present.

SUMMARY

An object of the present application is to provide a composition for removing phospholipids and cell debris and a method for removing phospholipids and cell debris on biological tissue. The composition of the present application is used for treating the biological tissue, and the treated biological tissue has an excellent anti-calcification effect.

In order to achieve the object described above, the present application adopts the following technical solutions.

1. A composition for removing phospholipids and cell debris, comprising an alcohol, an alcohol ether, and a surfactant, wherein the alcohol accounts for 50-90 wt %, preferably 60-80 wt %; the alcohol ether accounts for 5-40 wt %, preferably 10-20 wt %; the surfactant accounts for 0.1-5 wt %, preferably 1-3 wt %.
2. The composition according to item 1, consisting of an alcohol, an alcohol ether, a surfactant, and a buffer, wherein the alcohol accounts for 50-90 wt %, preferably 60-80 wt %; the alcohol ether accounts for 5-40 wt %, preferably 10-20 wt %; the surfactant accounts for 0.1-5 wt %, preferably 1-3 wt %; the buffer is the balance.
3. The composition according to item 1 or 2, wherein the alcohol is selected from one or two or more of methanol, ethanol, isopropanol, tert-butanol, ethylene glycol, propylene glycol, butylene glycol, diethylene glycol, or dipropylene glycol ester, preferably ethanol or isopropanol.
4. The composition according to item 1 or 2, wherein the alcohol ether is selected from one or two or more of ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, diethylene glycol monopropyl ether, diethylene glycol diethyl ether, diethylene glycol monobutyl ether, propylene glycol monomethyl ether, propylene glycol monoethyl ether, dipropylene glycol monomethyl ether, dipropylene glycol monoethyl ether, dipropylene glycol monopropyl ether, or dipropylene glycol monobutyl ether, preferably propylene glycol monomethyl ether or ethylene glycol monoethyl ether.
5. The composition according to item 1 or 2, wherein the surfactant is selected from one or two or more of alkylphenol polyoxyethylene ether, fatty alcohol polyoxyethylene ether, sodium dodecyl sulfate, sodium deoxycholate, EDTA, Triton X-100, or polysorbate, preferably sodium deoxycholate or polysorbate.
6. The composition according to item 2, wherein the buffer is a PBS buffer or a HEPES buffer.
7. A method for removing phospholipids and cell debris on biological tissue, comprising the following steps:

placing the biological tissue into the composition for removing phospholipids and cell debris according to any one of items 1 to 6 for treatment to give a roughly treated biological tissue;

placing the roughly treated biological tissue into a fixative solution for fixation treatment to give a fixed biological tissue; and placing the fixed biological tissue into a sterilization solution for sterilization treatment to give biological tissue from which the phospholipids and the cell debris are removed.

8. The method according to item 7, wherein the biological tissue is immersed in the composition for removing phospholipids and cell debris and subjected to shaking treatment, and not lower than 10 mL of the composition for removing phospholipids and cell debris is required per square centimeter of the biological tissue for treatment.
9. The method according to item 7, wherein the biological tissue is a pericardial material.
10. The method according to item 7, wherein the biological tissue is treated in the composition for removing phospholipids and cell debris at a temperature of ° C., preferably 25-35° C., for a treatment time of 1-48 h, preferably 18-36 h.
11. The method according to item 7, wherein the roughly treated biological tissue is subjected to the fixation treatment in the fixative solution at a temperature of ° C., preferably 40-50° C., for a treatment time of 1-14 d, preferably 2-6 d.
12. The method according to item 7, wherein the fixative solution is 1-ethyl-3-(3-dimethylaminopropyl) carbodiimide or glutaraldehyde and has a concentration of 0.1-1 wt %.
13. The method according to item 7, wherein the sterilization treatment is performed at a temperature of 20-50° C., preferably 35-45° C., for a treatment time of 1-48 h, preferably 18-36 h.

14. The method according to item 7, wherein the sterilization solution comprises wt % of an aldehyde and 10-30 wt % of an alcohol;

the aldehyde is one or two of formaldehyde or glutaraldehyde, and the alcohol is one or two or more of methanol, ethanol, isopropanol, ethylene glycol, and 1,2,3-propanetriol glycidyl ethers.

15. The method according to item 7, wherein the biological tissue from which the phospholipids and the cell debris are removed is stored in a product preservation solution comprising 0.1-1 wt % of glutaraldehyde.

According to the composition for removing phospholipids and cell debris of the present application, the alcohol, alcohol ether, and surfactant are intended to increase the solubility of the composition to phospholipids and cell debris with different polarities by the cooperation of the alcohol, alcohol ether, and surfactant, thereby removing more substances which are easy to cause calcification on the biological tissue. A phospholipid is amphiphilic because of containing a nonpolar alkyl chain and a polar phosphate group, and the amphiphilic properties of the phospholipids is significantly different due to different lengths of alkyl chains and different groups in the phospholipids. Common phosphatidyl choline has a good amphiphilic property and can be dissolved in alcohol solvents such as methanol and ethanol. However, sphingomyelin and lecithin have strong non-polarity and poor solubility in alcohol solvents, so that a reagent with stronger non-polarity needs to be selected for dissolution. In addition, the phospholipid is an important component of the cell membrane, and when the solution has relatively good solubility to the phospholipid, the removal of cells and cell debris can be achieved, so the composition obtained at a specific ratio has a good effect of removing phospholipids and cell debris, such that the biological tissue has a good anti-calcification effect.

DETAILED DESCRIPTION

The present application will be described in detail below.

The present application provides a composition for removing phospholipids and cell debris, comprising an alcohol, an alcohol ether, and a surfactant, wherein the alcohol accounts for 50-90 wt %, preferably 60-80 wt %; the alcohol ether accounts for 5-40 wt %, preferably 10-20 wt %; the surfactant accounts for 0.1-5 wt %, preferably 1-3 wt %.

The present application provides a composition for removing phospholipids and cell debris, consisting of an alcohol, an alcohol ether, a surfactant, and a buffer, wherein the alcohol accounts for 50-90 wt %, preferably 60-80 wt %; the alcohol ether accounts for 5-40 wt %, preferably 10-20 wt %; the surfactant accounts for 0.1-5 wt %, preferably 1-3 wt %; the buffer is the balance.

In the composition for removing phospholipids and cell debris of the present application, the alcohol, alcohol ether, and surfactant are intended to increase the solubility of the composition to phospholipids and cell debris with different polarities by the cooperation of the alcohol, alcohol ether, and surfactant, thereby removing more substances which are easy to cause calcification on the biological tissue. A phospholipid is amphiphilic because of containing a nonpolar alkyl chain and a polar phosphate group, and the amphiphilic properties of the phospholipids is significantly different due to different lengths of alkyl chains and different groups in the phospholipids. Common phosphatidyl choline has a good amphiphilic property and can be dissolved in alcohol solvents such as methanol and ethanol. However, sphingomyelin and lecithin have strong non-polarity and poor solubility in alcohol solvents, so that a reagent with stronger non-polarity needs to be selected for dissolution. In addition, the phospholipid is an important component of the cell membrane, and when the solution has relatively good solubility to the phospholipid, the removal of cells and cell debris can be achieved, so the composition obtained at a specific ratio has a good effect of removing phospholipids and cell debris, such that the biological tissue has a good anti-calcification effect.

In the present application, the content of the alcohol may be one of 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, and 90 wt %.

The content of the alcohol ether may be one of 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, and 40 wt %.

The content of the surfactant may be one of 0.1 wt %, 0.2 wt %, 0.3 wt %, 0.4 wt %, 0.5 wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, and 5 wt %.

The buffer is a conventional buffer, preferably a PBS buffer or a HEPES buffer.

In the present application, the alcohol is selected from one or two or more of methanol, ethanol, isopropanol, tert-butanol, ethylene glycol, propylene glycol, butylene glycol, diethylene glycol, or dipropylene glycol ester, preferably ethanol or isopropanol.

In the present application, the alcohol ether is selected from one or two or more of ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, diethylene glycol monopropyl ether, diethylene glycol diethyl ether, diethylene glycol monobutyl ether, propylene glycol monomethyl ether, propylene glycol monoethyl ether, dipropylene glycol monomethyl ether, dipropylene glycol monoethyl ether, dipropylene glycol monopropyl ether, or dipropylene glycol monobutyl ether, preferably propylene glycol monomethyl ether or ethylene glycol monoethyl ether.

In the present application, the surfactant is selected from one or two or more of alkylphenol polyoxyethylene ether, fatty alcohol polyoxyethylene ether, sodium dodecyl sulfate, sodium deoxycholate, EDTA, Triton X-100, or polysorbate, preferably sodium deoxycholate or polysorbate.

In the composition of the present application, when the alcohol is ethanol, the alcohol ether is propylene glycol monomethyl ether, and the surfactant may be sodium deoxycholate; the content of ethanol may be one of 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, and 90 wt %; the content of propylene glycol monomethyl ether may be one of 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, and 40 wt %; the content of sodium deoxycholate may be one of 0.1 wt %, 0.2 wt %, 0.3 wt %, 0.4 wt %, 0.5 wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, and 5 wt %.

In the composition of the present application, when the alcohol is isopropanol, the alcohol ether is propylene glycol monomethyl ether, and the surfactant may be sodium deoxycholate; the content of isopropanol may be one of 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, and 90 wt %; the content of propylene glycol monomethyl ether may be one of 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, and 40 wt %; the content of sodium deoxycholate may be one of 0.1 wt %, 0.2 wt %, 0.3 wt %, 0.4 wt %, 0.5 wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, and 5 wt %.

In the composition of the present application, when the alcohol is ethanol, the alcohol ether is propylene glycol monomethyl ether, and the surfactant may be sodium deoxycholate; the content of ethanol may be one of 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, and 90 wt %; the content of propylene glycol monomethyl ether may be one of 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, and 40 wt %; the content of sodium deoxycholate may be one of 0.1 wt %, 0.2 wt %, 0.3 wt %, 0.4 wt %, 0.5 wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, and 5 wt %.

In the composition of the present application, when the alcohol is ethanol, the alcohol ether is propylene glycol monomethyl ether, and the surfactant may be polysorbate; the content of ethanol may be one of 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, and 90 wt %; the content of propylene glycol monomethyl ether may be one of 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, and 40 wt %; the content of polysorbate may be one of 0.1 wt %, 0.2 wt %, 0.3 wt %, 0.4 wt %, wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, and 5 wt %.

In the composition of the present application, when the alcohol is ethanol, the alcohol ether is ethylene glycol monoethyl ether, and the surfactant may be polysorbate; the content of ethanol may be one of 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, and 90 wt %; the content of ethylene glycol monoethyl ether may be one of wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, and 40 wt %; the content of polysorbate may be one of 0.1 wt %, 0.2 wt %, 0.3 wt %, 0.4 wt %, wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, and 5 wt %.

In the composition of the present application, when the alcohol is polypropanol, the alcohol ether is ethylene glycol monoethyl ether, and the surfactant may be polysorbate; the content of polypropanol may be one of 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, and 90 wt %; the content of ethylene glycol monoethyl ether may be one of 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, and wt %; the content of polysorbate may be one of 0.1 wt %, 0.2 wt %, 0.3 wt %, wt %, 0.5 wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, and 5 wt %.

In the composition of the present application, when the alcohol is polypropanol, the alcohol ether is ethylene glycol monoethyl ether, and the surfactant may be sodium deoxycholate; the content of polypropanol may be one of 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, and 90 wt %; the content of ethylene glycol monoethyl ether may be one of 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, and 40 wt %; the content of sodium deoxycholate may be one of 0.1 wt %, wt %, 0.3 wt %, 0.4 wt %, 0.5 wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, and 5 wt %.

In the composition of the present application, when the alcohol is polypropanol, the alcohol ether is propylene glycol monomethyl ether, and the surfactant may be polysorbate; the content of polypropanol may be one of 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, and 90 wt %; the content of propylene glycol monomethyl ether may be one of 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 37 wt %, 38 wt %, 39 wt %, and 40 wt %; the content of polysorbate may be one of 0.1 wt %, 0.2 wt %, 0.3 wt %, 0.4 wt %, 0.5 wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, and 5 wt %.

The present application further provides a method for removing phospholipids and cell debris on biological tissue, comprising the following steps:

step 1: placing the biological tissue into the composition for removing phospholipids and cell debris for treatment to give a roughly treated biological tissue;

step 2: placing the roughly treated biological tissue into a fixative solution for fixation treatment to give a fixed biological tissue; and step 3: placing the fixed biological tissue into a sterilization solution for sterilization treatment to give biological tissue from which the phospholipids and the cell debris are removed.

In the present application, the biological tissue is a pericardial material, and may be, for example, porcine pericardium, bovine pericardium, or the like.

In step 1, the biological tissue is immersed in the composition for removing phospholipids and cell debris and subjected to shaking treatment, and not lower than 10 mL of the composition for removing phospholipids and cell debris is required per square centimeter of the surface area of the biological tissue for treatment (since the thickness of the biological tissue is usually less than 0.5 mm, the thickness thereof can be ignored, and the surface area is used to calculate the content of the treatment solution). The biological tissue is treated in the composition for removing phospholipids and cell debris at a temperature of 20-50° C., preferably 25-35° C., for a treatment time of 1-48 h, preferably 18-36 h.

Phospholipids and cell debris in the biological tissue are dissolved by the composition, thereby being removed from the biological tissue.

In step 2, the roughly treated biological tissue is immersed in the fixative solution and subjected to shaking treatment, and not lower than 10 mL of the fixative solution is required per square centimeter of the biological tissue for treatment. The roughly treated biological tissue is subjected to the fixation treatment in the fixative solution at a temperature of 20-50° C., preferably 40-50° C., for a treatment time of 1-14 d, preferably 2-6 d.

The fixation treatment may be performed in the fixative solution at a temperature of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

The fixation treatment may be performed in the fixative solution for a treatment time of 1 d, 2 d, 3 d, 4 d, 5 d, 6 d, 7 d, 8 d, 9 d, 10 d, 11 d, 12 d, 13 d, or 14 d.

The fixative solution is 1-ethyl-3-(3-dimethylaminopropyl) carbodiimide or glutaraldehyde and has a concentration of 0.1-1 wt %, and the balance is a PBS buffer or a HEPES buffer.

The fixative solution may enhance the cross-linking strength of tissues to ensure the mechanical performance.

In step 3, the sterilization treatment is performed at a temperature of 20-50° C., preferably 35-45° C., for a treatment time of 1-48 h, preferably 18-36 h.

The biological tissue from which the phospholipids and cell debris are removed is sterilized for further storage to prevent the biological tissue from being destroyed by bacteria.

The sterilization solution comprises 0.5-10 wt % of an aldehyde, 10-30 wt % of an alcohol, and the balance of a PBS buffer or a HEPES buffer;

the aldehyde is one or two of formaldehyde or glutaraldehyde, and the alcohol is one or two or more of methanol, ethanol, isopropanol, ethylene glycol, and 1,2,3-propanetriol glycidyl ethers.

In the present application, the biological tissue from which phospholipids and cell debris are removed is stored in a product preservation solution comprising 0.1-1 wt % of glutaraldehyde and the balance of a PBS buffer or a HEPES buffer.

The biological tissue is subjected to an anti-calcification test as follows: when the biological tissue is treated by the composition for removing phospholipids and cell debris of the present application, the treated biological tissue is implanted subcutaneously in a rat for 30 days, and the calcium ion content in the biological tissue is tested after 30 days. The results show that in the composition, when the alcohol accounts for 60-80 wt %, the alcohol ether accounts for 10-20 wt %, the surfactant accounts for 1-3 wt %, and the fixation treatment is performed at a temperature of 40-50° C., the calcium ion content in the biological tissue is relatively low, the calcium content is lower than 1 μg/mg, and the biological tissue has an excellent anti-calcification effect.

The following examples of the present application are intended only to illustrate specific embodiments for achieving the present application, and these embodiments are not to be construed as limiting the present application. Any other changes, modifications, substitutions, combinations, and simplifications made without departing from the spirit and principle of the present application are regarded as equivalent replacements and shall fall within the protective scope of the present application.

EXAMPLES

The experimental methods used in the following examples are all conventional methods unless otherwise specified.

The materials, reagents, and the like used in the following examples are all commercially available unless otherwise specified.

Example 1

6×6 cm porcine pericardium was placed into 360 mL of a composition for removing phospholipids and cell debris (the composition contained 50 wt % of ethanol, 40 wt % of propylene glycol monomethyl ether, 0.1 wt % of sodium deoxycholate, and the balance of a HEPES buffer) for treatment at a temperature of 40° C. for a treatment time of 24 h to give a roughly treated biological tissue; the roughly treated biological tissue was placed into 360 mL of a fixative solution (the fixative solution contained 1 wt % of glutaraldehyde and the balance of a PBS buffer) at 20° C. for 7 days to give a fixed biological tissue. The fixed biological tissue was placed into 360 mL of a sterilization solution (the sterilization solution contained 2 wt % of glutaraldehyde, 3 wt % of formaldehyde, 15 wt % of isopropanol, and the balance of a PBS buffer) for sterilization at a temperature of 50° C. for a sterilization time of 24 h to give biological tissue from which phospholipids and cell debris were removed; the biological tissue was subjected to an anti-calcification test (the specific procedures of the anti-calcification test were as follows: the treated pericardium was implanted subcutaneously in a rat for 30 days, the calcium ion content of the pericardium was tested after 30 days, and the anti-calcification performance was evaluated). The specific parameters are shown in Table 1.

Examples 2-9 and Comparative Examples 1-2 are different from Example 1 in the formulas of compositions for removing phospholipids and cell debris and in the treatment parameters, as detailed in Table 1.

Example 10 is different from Example 5 in the type of alcohol ether, as detailed in Table 1.

Example 11 is different from Example 4 in the type of alcohol, as detailed in Table 1.

Example 12 is different from Example 6 in the type of surfactant, as detailed in Table 1.

Examples 13-15 are different from Example 6 in the treatment temperature of step 2, as detailed in Table 1.

Comparative Example 3 is different from Example 4 in that Comparative Example 3 had no alcohol, as detailed in Table 1.

Comparative Example 4 is different from Example 5 in that Comparative Example 3 had no alcohol ether, as detailed in Table 1.

Comparative Example 5 is different from Example 6 in that Comparative Example 3 had no surfactant, as detailed in Table 1.

TABLE 1

Parameters of Examples and Comparative Examples

| | Alcohol | Alcohol ether | Surfactant | Treatment time in step 1/h | Treatment temperature in step 2/° C. | Calcium content of the rat implanted subcutaneously for 30 days μg/mg |
|---|---|---|---|---|---|---|
| Example 1 | 50% ethanol | 40% propylene glycol monomethyl ether | 0.1% sodium deoxycholate | 24 | 20 | 1.6 |
| Example 2 | 90% isopropanol | 5% propylene glycol monomethyl ether | 3.2% polysorbate | 24 | 50 | 1.8 |
| Example 3 | 85% isopropanol | 10% ethylene glycol monoethyl ether | 0.5% polysorbate | 24 | 30 | 1.2 |

TABLE 1-continued

Parameters of Examples and Comparative Examples

| | Alcohol | Alcohol ether | Surfactant | Treatment time in step 1/h | Treatment temperature in step 2/° C. | Calcium content of the rat implanted subcutaneously for 30 days μg/mg |
|---|---|---|---|---|---|---|
| Example 4 | 70% ethanol | 15% propylene glycol monomethyl ether | 1% sodium deoxycholate | 24 | 40 | 0.6 |
| Example 5 | 60% isopropanol | 20% ethylene glycol monoethyl ether | 2% polysorbate | 24 | 45 | 0.6 |
| Example 6 | 80% ethanol | 10% propylene glycol monomethyl ether | 2.5% polysorbate | 24 | 50 | 0.8 |
| Example 7 | 50% isopropanol | 10% propylene glycol monomethyl ether | 1% sodium deoxycholate | 24 | 25 | 1.3 |
| Example 8 | 85% ethanol | 7% ethylene glycol monoethyl ether | 0.5% sodium deoxycholate | 24 | 25 | 1.2 |
| Example 9 | 55% isopropanol | 35% propylene glycol monomethyl ether | 1.5% polysorbate | 24 | 30 | 1.4 |
| Example 10 | 60% isopropanol | 20% diethylene glycol monoethyl ether | 2% polysorbate | 24 | 45 | 1.2 |
| Example 11 | 70% tert-butanol | 15% propylene glycol monomethyl ether | 1% sodium deoxycholate | 24 | 40 | 1.5 |
| Example 12 | 80% ethanol | 10% propylene glycol monomethyl ether | 2.5% EDTA | 24 | 50 | 1.6 |
| Example 13 | 80% ethanol | 10% propylene glycol monomethyl ether | 2.5% polysorbate | 24 | 20 | 1.3 |
| Example 14 | 80% ethanol | 10% propylene glycol monomethyl ether | 2.5% polysorbate | 24 | 30 | 1.1 |
| Example 15 | 80% ethanol | 10% propylene glycol monomethyl ether | 2.5% polysorbate | 24 | 40 | 0.8 |
| Comparative Example 1 | 50% ethylene glycol | 5% ethylene glycol monoethyl ether | 0.1% polysorbate | 24 | 25 | 3.8 |
| Comparative Example 2 | 10% ethanol | 40% propylene glycol monomethyl ether | 10% sodium deoxycholate | 24 | 35 | 2.1 |
| Comparative Example 3 | 0% | 15% propylene glycol monomethyl ether | 1% sodium deoxycholate | 24 | 40 | 4.8 |
| Comparative Example 4 | 60% isopropanol | 0% | 2% polysorbate | 24 | 45 | 5.3 |
| Comparative Example 5 | 80% ethanol | 10% propylene glycol monomethyl ether | 0% | 24 | 50 | 4.1 |

Summary: Compared with no addition of alcohol ether reagents, after alcohol ether substances were added to the solution for removing phospholipids and cell debris, the calcium content of the whole pericardium of the rat implanted subcutaneously for 30 days was relatively low. Moreover, when the ratio of the alcohol, alcohol ether, and surfactant was appropriate, the calcium content after implantation for 30 days was lower than 1 μg/mg, showing an excellent anti-calcification effect.

The invention claimed is:

1. A method for removing phospholipids and cell debris on biological tissue, comprising the following steps:

placing the biological tissue into the composition for removing phospholipids and cell debris for treatment to give a roughly treated biological tissue; wherein the composition comprises an alcohol, an alcohol ether, and a surfactant, wherein, the alcohol accounts for 60-80 wt %, the alcohol ether accounts for 10-20 wt %, and the surfactant accounts for 1-3 wt %;

the alcohol is ethanol or isopropanol, the alcohol ether is one of propylene glycol monomethyl ether, ethylene glycol monoethyl ether, ethylene glycol monopropyl ether, diethylene glycol monomethyl ether, and dipropylene glycol monomethyl ether, and the surfactant is sodium deoxycholate or polysorbate;

placing the roughly treated biological tissue into a fixative solution for fixation treatment to give a fixed biological tissue; and placing the fixed biological tissue into a sterilization solution for sterilization treatment to give biological tissue from which the phospholipids and the cell debris are removed.

2. The method according to claim 1, wherein the biological tissue is immersed in the composition for removing phospholipids and cell debris and subjected to shaking treatment, and not lower than 10 mL of the composition for removing phospholipids and cell debris is required per square centimeter of the biological tissue for treatment.

3. The method according to claim 1, wherein the biological tissue is a pericardial material.

4. The method according to claim 1, wherein the biological tissue is treated in the composition for removing phospholipids and cell debris at a temperature of 20-50° C. for a treatment time of 1-48 h.

5. The method according to claim 4, wherein the biological tissue is treated in the composition for removing phospholipids and cell debris at a temperature of 25-35° C.

6. The method according to claim 4, wherein the biological tissue is treated in the composition for removing phospholipids and cell debris for a treatment time of 18-36 h.

7. The method according to claim 1, wherein the roughly treated biological tissue is subjected to the fixation treatment in the fixative solution at a temperature of 20-50° C. for a treatment time of 1-14 d.

8. The method according to claim 7, wherein the roughly treated biological tissue is subjected to the fixation treatment in the fixative solution at a temperature of 40-50° C.

9. The method according to claim 7, wherein the roughly treated biological tissue is subjected to the fixation treatment in the fixative solution for a treatment time of 2-6 d.

10. The method according to claim 1, wherein the fixative solution is 1-ethyl-3-(3-dimethylaminopropyl) carbodiimide or glutaraldehyde and has a concentration of 0.1-1 wt %.

11. The method according to claim 1, wherein the sterilization treatment is performed at a temperature of 20-50° C. for a treatment time of 1-48 h.

12. The method according to claim 11, wherein the sterilization treatment is performed at a temperature of 35-45° C.

13. The method according to claim 11, wherein the sterilization treatment is performed for a treatment time of 18-36 h.

14. The method according to claim 1, wherein the sterilization solution comprises 0.5-10 wt % of an aldehyde and 10-30 wt % of an alcohol;

the aldehyde is one or two of formaldehyde or glutaraldehyde, and the alcohol is one or two or more of methanol, ethanol, isopropanol, ethylene glycol, and 1,2,3-propanetriol glycidyl ethers.

15. The method according to claim 1, wherein the biological tissue from which the phospholipids and the cell debris are removed is stored in a product preservation solution comprising 0.1-1 wt % of glutaraldehyde.

* * * * *